(12) United States Patent
Lassen

(10) Patent No.: US 10,189,779 B2
(45) Date of Patent: Jan. 29, 2019

(54) METHODS FOR PRODUCING THIOL COMPOUNDS AND SULFIDE COMPOUNDS USING DIPHENYLAMINE OR A PHENOL COMPOUND

(71) Applicant: Chevron Phillips Chemical Company LP, The Woodlands, TX (US)

(72) Inventor: Kenneth M. Lassen, Bartlesville, OK (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 206 days.

(21) Appl. No.: 15/262,045

(22) Filed: Sep. 12, 2016

(65) Prior Publication Data

US 2018/0072663 A1  Mar. 15, 2018

(51) Int. Cl.
*C07C 319/18* (2006.01)
*B01J 19/12* (2006.01)
*C07C 319/04* (2006.01)

(52) U.S. Cl.
CPC ........... *C07C 319/18* (2013.01); *B01J 19/123* (2013.01); *C07C 319/04* (2013.01)

(58) Field of Classification Search
CPC .......................... C07C 319/04; C07C 319/18
See application file for complete search history.

(56) References Cited

U.S. PATENT DOCUMENTS

| | | | |
|---|---|---|---|
| 4,135,047 A | 1/1979 | Morgan | |
| 4,140,604 A | 2/1979 | Dimmig | |
| 4,443,310 A | 4/1984 | Arretz et al. | |
| 5,929,202 A | 7/1999 | Arita et al. | |
| 7,847,019 B2 | 12/2010 | David et al. | |
| 7,989,655 B2 | 8/2011 | Refvik et al. | |
| 8,461,293 B2 | 6/2013 | Matson et al. | |
| 8,765,984 B2 | 7/2014 | Upshaw | |
| 9,126,919 B2 | 9/2015 | Cazaux et al. | |
| 9,133,370 B2 | 9/2015 | Matson et al. | |
| 9,340,715 B2 | 5/2016 | Matson et al. | |
| 9,340,716 B2 | 5/2016 | Matson et al. | |
| 9,340,717 B2 | 5/2016 | Matson et al. | |
| 9,469,607 B2 | 10/2016 | Upshaw et al. | |
| 9,522,975 B2 | 12/2016 | Matson et al. | |
| 2012/0035291 A1 | 2/2012 | Matson et al. | |
| 2013/0190505 A1* | 7/2013 | Wu | C07B 45/06 548/251 |
| 2014/0221692 A1 | 8/2014 | Netemeyer | |

FOREIGN PATENT DOCUMENTS

GB 895993 5/1962

OTHER PUBLICATIONS

International Search Report and the Written Opinion of the International Searching Authority in PCT/US2017/050458 dated Nov. 20, 2017, 14 pages.
Keylor et al., entitled "*Photocatalytic initiation of thiol-ene reactions: synthesis of thiomorpholin-3-ones*," Tetrahedron, 2014, vol. 70, pp. 2464-2469.
Nicewicz et al., entitled "*Recent Applications of Organic Dyes as Photoredox Catalysts in Organic Synthesis*," ACS Catal., 2014, vol. 4, pp. 355-360.
Tyson et al., entitled "*Redox Mediators in Visible Light Photocatalysis: Photocatalytic Radical Thiol-Ene Additions*," J. Org. Chem., 2014, vol. 79, pp. 1427-1436.

\* cited by examiner

*Primary Examiner* — Kuo Liang Peng
(74) *Attorney, Agent, or Firm* — Merchant & Gould, P.C.

(57) ABSTRACT

The present invention discloses processes for producing a thiol compound or a sulfide compound from an olefin compound. Diphenylamine or a phenol compound can be used to increase the rate of conversion of the olefin compound to the thiol compound or the sulfide compound.

20 Claims, 1 Drawing Sheet

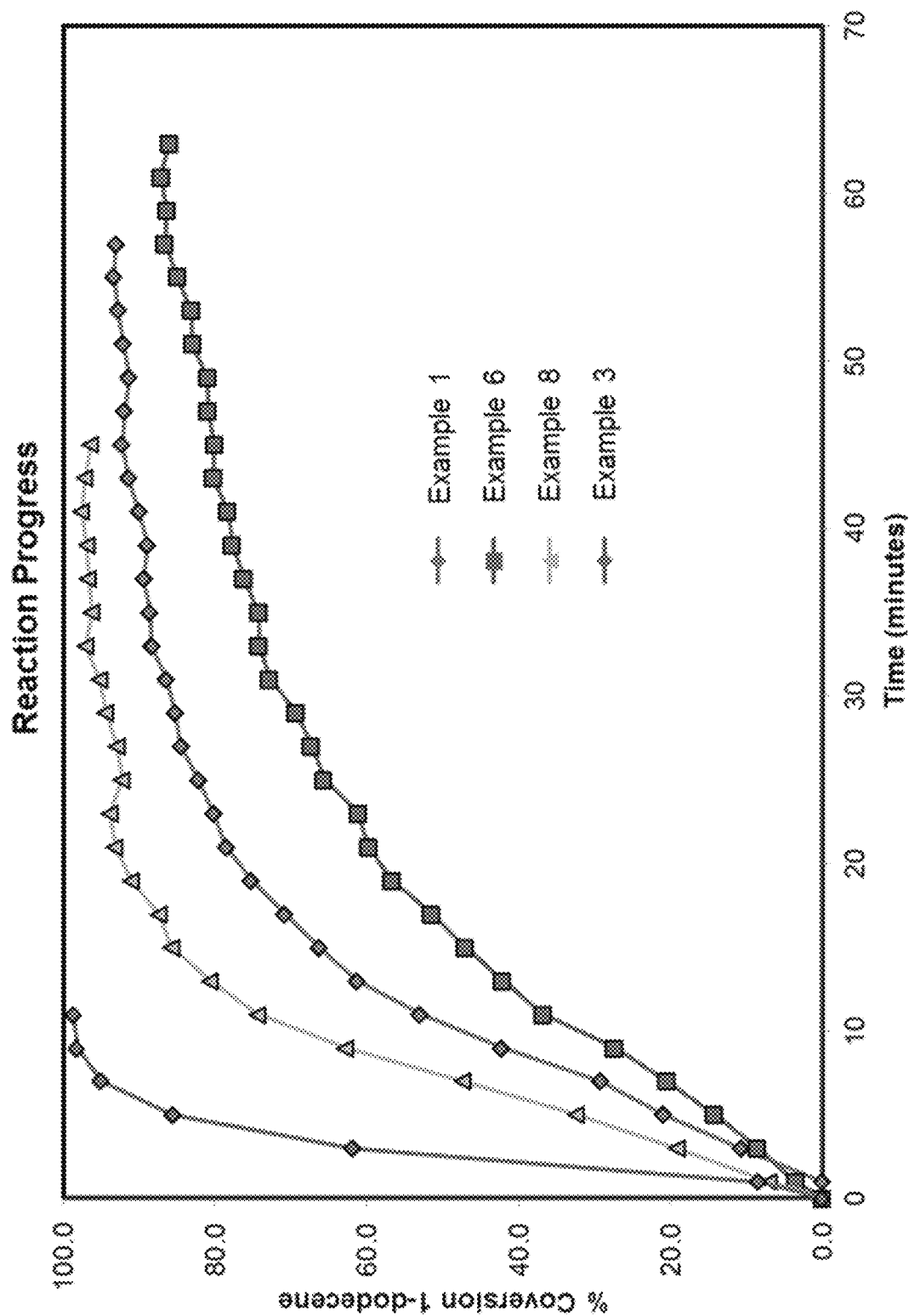

METHODS FOR PRODUCING THIOL COMPOUNDS AND SULFIDE COMPOUNDS USING DIPHENYLAMINE OR A PHENOL COMPOUND

BACKGROUND OF THE INVENTION

The present invention relates generally to processes for producing thiol compounds and sulfide compounds. Often, phosphite compounds—such as trimethylphosphite, triethylphosphite, and tributylphosphite—are used in these processes to scavenge elemental sulfur and to improve reaction efficiency and olefin conversion to the desired thiol compound or sulfide compound. However, these phosphite compounds can be difficult to separate from the desired reaction product, and additionally, can present waste disposal issues. Moreover, certain phosphite compounds are the subject of governmental regulation.

Thus, it would be beneficial to find suitable alternatives to phosphite compounds in processes for producing thiol compounds and sulfide compounds from olefins. Accordingly, it is to these ends that the present invention is principally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Various processes for producing thiol compounds are disclosed herein. One such process for producing a thiol compound can comprise (1) contacting (a) an olefin compound, (b) $H_2S$, (c) diphenylamine and/or a phenol compound (comprising BHT, carvacrol, 2,2'-ethylidene-bis(4,6-di-tert-butylphenol), pentaerythritol tetrakis(3,5-di-tert-butyl-4-hydroxyhydrocinnamate), or any combination thereof), and (d) a photoinitiator and/or a free radical initiator; and (2) forming the thiol compound. In general, the diphenylamine and/or the phenol compound can be used in the process at an amount ranging from about 0.05 wt. % to about 5 wt. % (or from about 0.1 wt. % to about 1 wt. %), based on the weight of the olefin compound; the molar ratio of $H_2S$ to carbon-carbon double bonds of the olefin compound can range from about 2:1 to about 500:1; and if present, the photoinitiator and/or the free radical initiator independently can be used at an amount ranging from about 0.05 wt. % to about 5 wt. % (or from about 0.1 wt. % to about 1 wt. %), based on the weight of the olefin compound.

Various processes for producing a sulfide compound also are disclosed herein. One such process for producing a sulfide compound can comprise (I) contacting (A) an olefin compound, (B) a mercaptan compound, and (C) diphenylamine and/or a phenol compound (comprising BHT, carvacrol, 2,2'-ethylidene-bis(4,6-di-tert-butylphenol), pentaerythritol tetrakis(3,5-di-tert-butyl-4-hydroxyhydrocinnamate), or any combination thereof); and (II) forming the sulfide compound. The mercaptan compound can have any suitable number of carbon atoms and any suitable number of —SH groups.

Beneficially, the conversion of the olefin compound to the thiol compound (or to the sulfide compound) can be greater than the conversion obtained by conducting the processes disclosed herein without diphenylamine and/or a phenol compound, under the same reaction conditions. The conversion is based on the conversion of carbon-carbon double bonds of the olefin compound to a sulfur-containing group (e.g., a thiol group or a sulfide group).

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE DRAWING

FIG. 1 presents a plot of the molar olefin conversion as a function of time for Examples 1, 3, 6, and 8.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects, a combination of different features can be envisioned. For each and every aspect and each and every feature disclosed herein, all combinations that do not detrimentally affect the designs, processes, and/or methods described herein are contemplated with or without explicit description of the particular combination. Additionally, unless explicitly recited otherwise, any aspect and/or feature disclosed herein can be combined to describe inventive features consistent with the present disclosure.

While processes are described herein in terms of "comprising" various steps, the processes can also "consist essentially of" or "consist of" the various steps, unless stated otherwise. For example, a process for producing a thiol compound consistent with aspects of the present invention can comprise; alternatively, can consist essentially of; or alternatively, can consist of; contacting an olefin compound, $H_2S$, diphenylamine and/or a phenol compound, and a photoinitiator and/or a free radical initiator to form a thiol compound.

The terms "a," "an," and "the" are intended to include plural alternatives, e.g., at least one. For instance, the disclosure of "an olefin compound" or "a phenol compound" is meant to encompass one, or mixtures or combinations of more than one, olefin compound or phenol compound, respectively, unless otherwise specified.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans,trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

A chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials having three or more hydrogen atoms, as necessary for the situation, removed from an alkane. The disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "hydrocarbyl group" is used herein in accordance with the definition specified by IUPAC: a univalent group formed by removing a hydrogen atom from a hydrocarbon (i.e., containing only carbon and hydrogen). Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic, and/or linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene groups, alkyl, alkylene, alkane groups, cycloalkyl, cycloalkylene, cycloalkane groups, alkylaryl/arylalkyl, aralkylene, and aralkane groups, respectively, amongst other groups as members.

The olefin compounds disclosed herein have at least one carbon-carbon double bond (e.g., compounds having one carbon-carbon double bond, two carbon-carbon double bonds, three carbon-carbon double bonds, etc.). These carbon-carbon double bonds (e.g., —C=C—), or olefinic double bonds, are non-aromatic double bonds, but the carbon-carbon double bonds can be located at any position (e.g., terminally or internally) in the olefin compound, unless specified otherwise or the context requires otherwise.

An aliphatic compound is an acyclic or cyclic, saturated or unsaturated compound, excluding aromatic compounds. That is, an aliphatic compound is a non-aromatic organic compound. Aliphatic compounds, and therefore aliphatic groups, can contain organic functional group(s) and/or atom(s) other than carbon and hydrogen. An "aliphatic group" is a generalized group formed by removing one or more hydrogen atoms (as necessary for the particular group) from a carbon atom of an aliphatic compound.

The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic, and/or linear or branched, unless otherwise specified. Primary, secondary, or tertiary alkyl groups are derived by removal of a hydrogen atom from a primary, secondary, or tertiary carbon atom, respectively, of an alkane. The n-alkyl group is derived by removal of a hydrogen atom from a terminal carbon atom of a linear alkane. The groups $RCH_2$ ($R \neq H$), $R_2CH$ ($R \neq H$), and $R_3C$ ($R \neq H$) are primary, secondary, and tertiary alkyl groups, respectively.

A cycloalkane is a saturated cyclic hydrocarbon, with or without side chains, for example, cyclobutane and methylcyclobutane. Unsaturated cyclic hydrocarbons having one endocyclic double or one triple bond are called cycloalkenes and cycloalkynes, respectively. Those having more than one such multiple bond are cycloalkadienes, cycloalkatrienes, and so forth. A "cycloalkyl group" is a univalent group derived by removing a hydrogen atom from a ring carbon atom from a cycloalkane. For example, a 1-methylcyclopropyl group and a 2-methylcyclopropyl group are illustrated as follows:

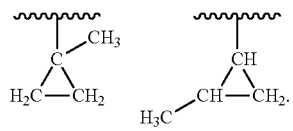

Similarly, a "cycloalkylene group" refers to a group derived by removing two hydrogen atoms from a cycloalkane, at least one of which is a ring carbon. Thus, a "cycloalkylene group" includes a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane.

The terms "contact product," "contacting," and the like, are used herein to describe methods and compositions wherein the components are contacted together in any order, in any manner, and for any length of time, unless stated otherwise. For example, the components can be contacted by blending or mixing. Further, unless otherwise specified, the contacting of any component can occur in the presence or absence of any other component of the methods and compositions described herein. Combining additional materials or components can be done by any suitable technique. Further, the term "contact product" includes mixtures, blends, solutions, slurries, reaction products, and the like, or combinations thereof. Although "contact product" can, and often does, include reaction products, it is not required for the respective components to react with one another. Likewise, "contacting" two or more components can result in a reaction product or a reaction mixture. Consequently, depending upon the circumstances, a "contact product" can be a mixture, a reaction mixture, or a reaction product.

As used herein, "sulfur-containing compound" refers to a compound comprising at least one sulfur atom. Similarly, "thiol compound" refers to a compound comprising at least one thiol group as a subset of sulfur-containing compounds. Thus, a "thiol compound" can comprise a single thiol group, or two or more thiol groups (e.g., 2, 3, 4, 5, etc., thiol groups). Compounds comprising more than one thiol group also can be referred to as polythiol compounds, as a subset of the more general class of thiol compounds. Similarly, "sulfide compound" refers to a compound comprising at least one sulfide group. Thus, "sulfide compound" can describe compounds comprising a single sulfide group, but may also describe compounds comprising two or more sulfide groups (e.g., 2, 3, 4, 5, etc. sulfide groups). Compounds comprising more than one sulfide group also can be referred to as polysulfide compounds, as a subset of the more general class of sulfide compounds. Further, thiol compounds and sulfide compounds can contain any number of other functional groups (e.g., alcohols, amines, thiols, sulfides, etc.), unless explicitly limited.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

Applicant discloses several types of ranges in the present invention. When Applicant discloses or claims a range of any type, Applicant's intent is to disclose or claim individually each possible number that such a range could reasonably encompass, including end points of the range as well as any sub-ranges and combinations of sub-ranges encompassed therein. For example, when the Applicant discloses or claims a chemical moiety having a certain number of carbon atoms, Applicant's intent is to disclose or claim individually every possible number that such a range could encompass, consistent with the disclosure herein. For example, the disclosure that a moiety is a hydrocarbyl group having from 1 to 18 carbon atoms (i.e., a $C_1$-$C_{18}$ hydrocarbyl group), as used herein, refers to a moiety that can be selected independently from a hydrocarbyl group having 1, 2, 3, 4, 5, 6, 7, 8, 9, 10, 11, 12, 13, 14, 15, 16, 17, or 18 carbon atoms, as well as any range between these two numbers (for example, a hydrocarbyl group having 3 to 8 carbon atoms), and also including any combination of ranges between these two numbers (for example, a hydrocarbyl group having 1 to 4 carbon atoms and a hydrocarbyl group having 8 to 12 carbon atoms).

Applicant reserves the right to proviso out or exclude any individual members of any such group, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any individual substituents, analogs, compounds, ligands, structures, or groups thereof, or any members of a claimed group, if for any reason Applicant chooses to claim less than the full measure of the disclosure, for example, to account for a reference that Applicant may be unaware of at the time of the filing of the application.

DETAILED DESCRIPTION OF THE INVENTION

The present invention provides processes for producing thiol compounds and sulfide compounds in the presence of diphenylamine and/or a phenol compound. Beneficially, such processes demonstrate increased olefin conversion rates and faster reaction times than reactions performed without diphenylamine or the phenol compound present. Unexpectedly, in certain aspects, the processes utilizing diphenylamine and/or a phenol compound disclosed herein have conversion rates comparable to those achieved in processes that use phosphite compounds. Moreover, in certain instances, the reaction time required for the processes disclosed herein to reach a target conversion level was similar to that of the reaction times of analogous processes that were performed with phosphite compounds. Thus, the processes disclosed herein can have comparable performance to similar processes using phosphite compounds, while avoiding detrimental processing and workup issues, waste disposal concerns, and government regulations often associated with the use of phosphite compounds.

Processes for Producing Thiol Compounds

In accordance with certain aspects of this invention, a process to produce a thiol compound can comprise contacting an olefin compound (e.g., any of the olefin compounds disclosed herein having one carbon-carbon double bond, two carbon-carbon double bonds, etc.), $H_2S$, diphenylamine and/or a phenol compound, and a photoinitiator and/or a free radical initiator; and forming the thiol compound. The phenol compound can comprise butylated hydroxytoluene (BHT, dibutylhydroxytoluene), carvacrol, 2,2'-ethylidene-bis(4,6-di-tert-butylphenol), pentaerythritol tetrakis(3,5-di-tert-butyl-4-hydroxyhydrocinnamate), or any combination thereof. BHT (left) and carvacrol (right) have the following structures:

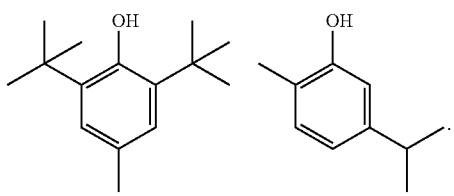

The phenol compound, 2,2'-ethylidene-bis(4,6-di-tert-butylphenol), has the following structure:

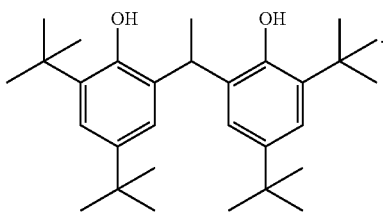 [SMILES: CC(c1cc(C(C)(C)C)cc(C(C)(C)C)c1O)c1cc(C(C)(C)C)cc(C(C)(C)C)c1O]

The phenol compound, pentaerythritol tetrakis(3,5-di-tert-butyl-4-hydroxyhydrocinnamate) has the following structure:

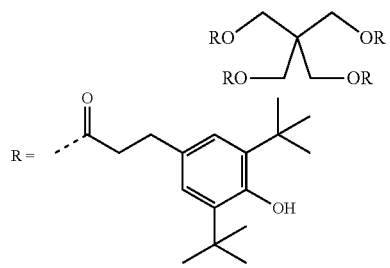

Generally, the features of the process (e.g., the olefin compound, the amount of diphenylamine and/or the phenol compound, the photoinitiator and/or free radical initiator, the hydrogen sulfide to carbon-carbon double bond molar ratio, and the conditions under which the thiol compound is formed, among others) are independently described herein and these features can be combined in any combination to further describe the disclosed process. Thiol compounds produced by any of these processes also are encompassed herein.

In certain aspects, the contacting step (step 1 of the process) can include contacting an olefin compound, $H_2S$, diphenylamine and/or a phenol compound, a photoinitiator and/or free radical initiator, and additional unrecited materials (e.g., a solvent). In other aspects, the contacting step can consist essentially of contacting the olefin compound, $H_2S$, diphenylamine and/or the phenol compound, and the photoinitiator and/or free radical initiator or, alternatively, can consist of contacting the olefin compound, $H_2S$, diphenylamine and/or the phenol compound, and the photoinitiator and/or free radical initiator. Likewise, additional materials or features can be employed in the forming step (step 2 of the process). For instance, the formation of the thiol compound can occur in the presence of ultraviolet (UV) light, discussed further hereinbelow. Moreover, it is contemplated that the processes for forming a thiol compound can employ more than one olefin compound. Additionally or alternatively, the processes for forming a thiol compound can employ two or more phenol compounds, or diphenylamine in combination with a phenol compound.

In the processes disclosed herein, the molar ratio of $H_2S$ to carbon-carbon double bonds of the olefin compound is not limited to any particular range. In some aspects, however, the minimum molar ratio of $H_2S$ to carbon-carbon double bonds of the olefin compound can be about 2:1, about 3:1, about 5:1, about 8:1, about 10:1, about 15:1, about 20:1, or about 25:1, while the maximum molar ratio of $H_2S$ to carbon-carbon double bonds of the olefin compound can be about 500:1, about 250:1, about 150:1, about 100:1, about 75:1, about 50:1 or about 35:1. Accordingly, suitable ranges for the ratio of $H_2S$ to carbon-carbon double bonds of the olefin compound can include, but are not limited to, the following: from about 2:1 to about 500:1, from about 2:1 to about 150:1, from about 2:1 to about 50:1, from about 3:1 to about 50:1, from about 10:1 to about 50:1, from about 5:1 to about 35:1, from about 8:1 to about 25:1, or from about 25:1 to about 250:1. Generally, an increase in the ratio of $H_2S$ to carbon-carbon double bonds of the olefin compound can lead to an increase in the percent conversion of the carbon-carbon double bonds to thiol groups. In contrast, a decrease in the ratio of $H_2S$ to carbon-carbon double bonds of the olefin compounds generally can lead to a decrease in the percent conversion of the carbon-carbon double bonds to thiol groups.

Generally, the amount of diphenylamine and/or the phenol compound utilized in the process for producing a thiol compound is not particularly limited. However, in one aspect, the amount of diphenylamine and/or the phenol compound, based on the weight of the olefin compound, can be in a range from about 0.05 wt. % to about 5 wt. %, from about 0.05 wt. % to about 3 wt. %, or from about 0.05 wt. % to about 1 wt. %. In another aspect, the amount of diphenylamine and/or the phenol compound can be in a range from about 0.1 wt. % to about 4 wt. %, from about 0.1 wt. % to about 2 wt. %, from about 0.1 wt. % to about 1 wt. %, or from about 0.2 wt. % to about 0.5 wt. %. In yet another aspect, the amount of diphenylamine and/or the phenol compound can be in a range from about 0.25 wt. % to about 2 wt. %, from about 0.25 wt. % to about 1.5 wt. %, from about 0.25 wt. % to about 1 wt. %, or from about 0.5 wt. % to about 1 wt. %.

While not limited thereto, a photoinitiator can be used at a minimum of about 0.05 wt. %, about 0.1 wt. %, about 0.2 wt. %, or about 0.3 wt. %, based on the weight of the olefin compound, and a maximum of about 0.5 wt. %, about 0.8 wt. %, about 1.0 wt. %, about 2 wt. %, or about 5 wt. %, based on the weight of the olefin compound. Generally, suitable ranges for the amount of the photoinitiator used in the process for producing a thiol compound can include, but are not limited to, the following: from about 0.05 wt. % to about 5 wt. %, from about 0.1 wt. % to about 5 wt. %, from about 0.05 wt. % to about 2 wt. %, from about 0.1 wt. % to about 2 wt. %, from about 0.1 wt. % to about 1 wt. %, from about 0.2 wt. % to about 1 wt. %, from about 0.05 wt. % to about 0.8 wt. %, or from about 0.2 wt. % to about 0.8 wt. %, based on the weight of the olefin compound.

While not limited thereto, a free radical initiator can be used at a minimum of about 0.05 wt. %, about 0.1 wt. %, about 0.2 wt. %, or about 0.3 wt. %, based on the weight of the olefin compound, and a maximum of about 0.5 wt. %, about 0.8 wt. %, about 1.0 wt. %, about 2 wt. %, or about 5 wt. %, based on the weight of the olefin compound. Generally, suitable ranges for the amount of the free radical initiator used in the process for producing a thiol compound can include, but are not limited to, the following: from about 0.05 wt. % to about 5 wt. %, from about 0.1 wt. % to about 5 wt. %, from about 0.05 wt. % to about 2 wt. %, from about 0.1 wt. % to about 2 wt. %, from about 0.1 wt. % to about 1 wt. %, from about 0.2 wt. % to about 1 wt. %, from about 0.05 wt. % to about 0.8 wt. %, or from about 0.2 wt. % to about 0.8 wt. %, based on the weight of the olefin compound.

In one aspect of this invention, a photoinitiator can be used in the process for producing a thiol compound, while in another aspect, a free radical initiator can be used in the process for producing a thiol compound, while in yet another aspect, a photoinitiator and a free radical initiator can be used in the process for producing a thiol compound.

Independently, steps 1 and 2 of the process for forming a thiol compound can be conducted at a variety of temperatures, pressures, and time periods. For instance, the temperature at which the olefin compound, $H_2S$, diphenylamine and/or the phenol compound, and the photoinitiator and/or free radical initiator are initially contacted can be the same as, or different from, the temperature at which the thiol compound is formed. As an illustrative example, in step 1, the olefin compound, $H_2S$, diphenylamine and/or the phenol compound, and the photoinitiator and/or free radical initiator can be contacted initially at temperature T1 and, after this initial combining, the temperature can be increased to a temperature T2 to allow the formation of the thiol compound. Likewise, the pressure can be different in step 1 than in step 2. Often, the time period in step 1 is referred to as the contact time, while the time period in step 2 is referred to as the reaction time. The contact time and the reaction time can be, and usually are, different.

In an aspect, step 1 of the process for forming a thiol compound can be conducted at a temperature in a range from about −30° C. to about 150° C.; alternatively, from about −20° C. to about 130° C.; alternatively, from about 15° C. to about 100° C.; alternatively, from about −5° C. to about 80° C.; alternatively, from about 20° C. to about 50° C.; or alternatively, from about 0° C. to about 60° C. In these and other aspects, after the initial contacting, the temperature can be changed, if desired, to another temperature for the formation of the thiol compound. Accordingly, step 2 can be conducted at a temperature in a range from about −30° C. to about 150° C.; alternatively, from about −20° C. to about 130° C.; alternatively, from about 15° C. to about 100° C.; alternatively, from about −5° C. to about 80° C.; alternatively, from about 20° C. to about 50° C.; or alternatively, from about 0° C. to about 60° C. These temperature ranges also are meant to encompass circumstances where the forming step can be conducted at a series of different temperatures, instead of at a single fixed temperature, falling within the respective ranges.

In an aspect, step 1 and/or step 2 of the process of forming a thiol compound can be conducted at a total reactor pressure in a range from about 30 to about 1500 psig (201-10342 kPag), such as, for example, from about 50 to about 1500 psig (345-10345 kPag). In some aspects, the thiol compound formation in step 2 can be conducted at total reactor pressure in a range from about 50 to about 1500 psig (345-10345 kPag); alternatively, from about 50 to about 1000 psig (345-6895 kPag); alternatively, from about 50 to about 750 psig (345-5171 kPag); alternatively, from about 50 to about 500 psig (345-3447 kPag); or alternatively, from about 100 to about 500 psig (689-3447 kPag).

The contact time in step 1 of the process is not limited to any particular range. That is, the olefin compound, $H_2S$, diphenylamine and/or the phenol compound, and the photoinitiator and/or free radical initiator can be initially contacted rapidly, or over a longer period of time, before commencing the reaction and/or the formation of the thiol compound in step 2. Hence, step 1 can be conducted, for example, in a time period ranging from as little as from about 1-30 seconds to as long as about 1-6 hours. In certain aspects, the contact time can be in a range from about 15 minutes to about 3 hours, or from about 30 minutes to about 2 hours. The appropriate reaction time for the formation of the thiol compound in step 2 can depend upon, for example, the reaction temperature and the molar ratios of the respective components in step 1, among other variables. However, the thiol compound often can be formed over a time period in step 2 that can be in a range from about 1 minute to about 8 hours, such as, for example, from about 2 minutes to about 6 hours, from about 5 minutes to about 5 hours, from about 10 minutes to about 4 hours, or from about 15 minutes to about 3 hours.

In aspects of this invention, once the olefin compound, $H_2S$, diphenylamine and/or the phenol compound, and the photoinitiator and/or free radical initiator are contacted, the thiol compound can be formed in the presence of electromagnetic radiation. For instance, the thiol compound can be formed in the presence of ultraviolet light. Additionally or alternatively, the thiol compound can be formed by light photolysis initiation of a free radical initiator. Additionally or alternatively, the thiol compound can be formed under conditions suitable for the thermal decomposition of a free radical initiator. Additionally, a photoinitiator can be utilized in conjunction with ultraviolet light or light photolysis initiation of a free radical initiator. Free radicals, therefore, can be generated in situ by a suitable energy source, or can be generated by the thermal decomposition of a free radical initiator, or by a combination of these sources. The thiol compound can be formed in the presence of free radicals from any one of aforementioned sources, including combinations thereof, but is not limited to free radicals generated only by these means.

In an aspect, the step 1 contacting of the olefin compound, $H_2S$, diphenylamine and/or the phenol compound, and the photoinitiator and/or free radical initiator can be conducted prior to the generation of free radicals and the formation of the thiol compound in step 2.

When the thiol compound is formed in the presence of ultraviolet light, ultraviolet light in the range, for example, from about 172 to about 450 nm, from about 172 to about 380 nm, or from about 172 to about 320 nm, can be employed. Ultraviolet light can be supplied from ultraviolet lamps, but other sources of ultraviolet light can be employed, and are to be considered within the scope of the present invention.

The photoinitiator can be any suitable photoinitiator. Generally, the photoinitiator can be any compound that produces or propagates a chemically reactive species upon exposure to light (e.g., visible light, ultraviolet light, etc.). For example, certain compounds comprising a ketone functionality can absorb a photon leading to fragmentation of the ketone bond and release of a free radical. Illustrative commercially available photoinitiators include, by way of example, Irgacure® 184 (1-hydroxy-cyclohexyl-phenyl-ketone), Irgacure® 500 (50% 1-hydroxy-cyclohexyl-phenyl-ketone and 50% b enzophenone), Irgacure® 819 (Bi s-(2, 4,6-trimethylbenzoyl)-phenylphosphineoxide), and Irgacure® 127 (2-hydroxy-1-{4-[4-(2-hydroxy-2-methyl-propionyl)-benzyl]-phenyl}-2-methyl-propan-1-one), all available from BASF, and Duracure 1173 (2-hydroxy-2-methyl-1-phenyl-1-propanone).

In certain aspects, the free radical initiator can be any free radical initiator capable of forming free radicals under thermal decomposition or light photolysis. For example, the free radical initiator employed for the formation of the thiol compound can comprise a —N=N— group, a —O—O— group, or combinations thereof; alternatively, a —N=N— group; or alternatively, a —O—O— group. Free radical initiators, therefore, can include, but are not limited to, peroxy compounds, organic azo compounds, or combinations thereof; alternatively, peroxy compounds; or alternatively, organic azo compounds. Peroxy compounds which can be utilized can include peroxides, hydroperoxides, peroxyesters, diacylperoxides, and percarbonates; alternatively, peroxides; alternatively, hydroperoxides; alternatively, peroxyesters; alternatively, diacylperoxides; or alternatively, percarbonates. In an aspect, the peroxide can be a dialkyl peroxide. In an aspect, the hydroperoxide can be an alkyl hydroperoxide. In an aspect, the peroxy ester can be an alkyl peroxyalkanoate, or alternatively, an alkyl peroxyarenoate. In an aspect, the diacylperoxide can be a diaroyl peroxide, or alternatively, a diakoyl peroxide. In an aspect, the percarbonate can be a dihydrocarbyl percarbonate; alternatively, a diarylpercarbonate; or alternatively, a dialkylpercarbonate. Generally, the hydrocarbon and/or alkane group(s) utilized in any peroxy compound can be a $C_1$ to $C_{30}$, $C_2$ to $C_{18}$, $C_2$ to $C_{10}$, or $C_2$ to $C_5$ hydrocarbon and/or alkane group(s). Generally, the arene group utilized in any peroxy compound can be a $C_6$ to $C_{30}$, $C_6$ to $C_{18}$, $C_6$ to $C_{15}$, or $C_6$ to $C_{10}$ arene group(s). Illustrative non-limiting examples of peroxy compounds which can be utilized can include, but are not limited to, diisobutyryl peroxide, 1-(2-ethylhexanoylperoxy)-1,3-dimethylbutyl peroxypivalate, cumylperoxyneodecanoate, 1,1,3,3-tetramethylbutyl peroxyneodecanoate, t-butyl peroxyneodecanoate, 1,1,3,3-tetramethylbutyl peroxypivalate, t-butyl peroxyneoheptanoate, t-amyl peroxypivalate, t-butyl peroxypivalate, di(3,5,5-trimethylhexanoyl) peroxide, dilauroyl peroxide, didecanoyl peroxide, 2,5-dimethyl-2,5-di(2-ethylhexanoylperoxy) hexane, 1,1,3,3-tetramethylbutyl peroxy 2-ethylhexanoate, t-amyl peroxy 2-ethylhexanoate, dibenzoyl peroxide, acetyl peroxide t-butyl peroxy 2-ethylhexanoate, t-butyl peroctanoate, t-butyl peroxydiethyl acetate, t-butyl peroxyisobutyrate, t-butyl peroxy 3,5,5-trimethylhexanoate, t-butyl peroxyacetate, t-butyl peoxybenzoate, 2,4-dichlorobenzoyl peroxide, t-butylpermaleic acid, di -t-butyl diperphthalate, di(4-t-butylcyclohexyl) peroxydicarbonate, di(2-ethylhexyl) peroxydicarbonate, dibutyl peroxydicarbonate, dicetyl peroxydicarbonate, dimyristyl peroxydicarbonate, t-amylperoxy 2-ethylhexyl carbonate, t-butylperoxy isopropyl carbonate, t-butylperoxy 2-ethylhexyl carbonate, 1,1-di(t-butylperoxy) 3,5,5-trimethylcyclohexane, 2,2-di(4,4-di(t-butylperoxy)cyclohexyl)propane, 1,1-di(t-butylperoxy) cyclohexane, 2,2-di(t-butylperoxy)butane, di(t-amyl) peroxide, dicumyl peroxide, di(t-butylperoxyisopropyl) benzene, 2,5-dimethyl-2,5-di(t-butylperoxy)hexane, t-butyl cumyl peroxide, 2,5-dimethyl-2,5-di(t-butylperoxy)hexyne-3, di-t-butyl peroxide, 3,6, 9-triethyl-3,6,9-trimethyl-1,4,7-triperoxoane, t-butyl hydroperoxide, methyl benzyl hydroperoxide, octylperbenzoate, methyl ethyl ketone peroxide, acetone peroxide, or combinations thereof.

Non-limiting examples of suitable azo compounds include α,α'-azo diisobutyronitrile (AIBN), azobenzene, azomethane, 2,2'-azodi(2-methylbutyronitrile), 2,2'-azobis(4-methoxy-2,4-dimethyl valeronitrile), dimethyl 2,2'-azobis(2-methylpropionate), 1,1'-azobis-(cyclohexane-1-carbonitrile), 1-[(cyano-1-methylethyl)azo] formamide, 2,2'-azobis(N-cyclohexyl-2-methylpropionamide), 2,2'-azobis (2,4-dimethyl valeronitrile), 2,2'-azobis(2-methylbutyronitrile), 2,2'-azobis[N-(2-propenyl)-2-methylpropionamide], 2,2'-azobis(N-butyl -2-methylpropionamide), 2,2'-azobis{2-methyl-N-[1,1-bis (hydroxymethyl)-2-hydroxy-ethyl] propionamide, 2,2'-azobis[2-methyl-N-(2-hydroxyethyl)propionamide], 2,2'-azobis [2-(2-imidazolin-2-yl)propane], 2,2'-azobis{2-methyl-N-[2-(1-hydroxybutyl)] propionamide}, 2,2'-azobis(2-methylpropionitrile), 4,4'-azobis(4-cyanovaleric acid), 2,2'-azobis(2-methylpropane), 2,2'-azobis(2-methylpropanamidine)dihydrochloride, methylpropionitrile, azodicarboxamide, or combinations thereof.

Generally, the peroxide and azo compound free radical initiators that can be utilized in accordance with the present invention decompose under first order kinetics. Skilled artisans can readily find the first order kinetic parameters which can be utilized to describe the decomposition of a particular free radical catalyst from sources such as chemical suppliers, industry reference publications, and/or open literature publications. Under first order kinetics, the time required for a given fraction (or percentage) of the free radical initiator to decompose, at a specific temperature, into initiating species is independent of the concentration of the free radical. This phenomenon is often stated as a half-life; that is, the time in which one-half of the free radical initiator decomposes under specific conditions (e.g., temperature). According to the first order kinetics, the half-life of a free radical initiator is defined as the time it takes one-half of the initiator to decompose at a particular temperature. Using the available first order kinetic parameters for a particular free radical initiator, the concentration of the free radical initiator present in the reaction mixture can be determined at a particular time during the reaction based upon the knowledge of the amount of free radical initiator added to the reaction, the times at which additional (if any) free radical initiator is added to the reaction, and the temperature profile of the reaction.

When the thiol compound is formed under conditions utilizing the thermal decomposition of a free radical initiator, the thiol compound can be formed at a temperature within a temperature range of the 1 hour half-life of the free radical initiator. Alternatively, when the thiol compound is formed under conditions utilizing the thermal decomposition of a free radical initiator, the thiol compound can be formed using a free radical initiator having a half-life within a time range at the temperature utilized to form the thiol compound. For example, step 2 of the process (the formation of the thiol compound) can be conducted at a temperature within ±25° C. of the 1 hour half-life of the free radical initiator. In other aspects, the thiol compound can be formed at a temperature within ±20° C. of the 1 hour half-life of the free radical initiator; alternatively, at a temperature within ±15° C. of the 1 hour half-life of the free radical initiator; alternatively, at a temperature within ±10° C. of the 1 hour half-life of the free radical initiator. In another aspect, the thiol compound can be formed using a free radical initiator having a half-life within a range from about 0.1 to about 10 hours at the temperature the thiol compound is formed (i.e., in step 2 of the process). Alternatively, the thiol compound can be formed using a free radical initiator having a half-life ranging from about 0.1 to about 10 hours, from about 0.25 to about 4 hours, or from about 0.5 to about 2 hours, at the temperature the thiol compound is formed. As above, in some aspects of this invention, the thiol compound can be formed at a temperature in a range from about 0° C. to about 120° C.; alternatively, from about 10° C. to about 110° C.; alternatively, from about 15° C. to about 100° C.; alternatively, from about 20° C. to about 100° C.; alternatively, from about 20° C. to about 80° C.; or alternatively, from about 25° C. to about 80° C.

Depending upon the particular free radical initiator, a free radical initiator can produce a different number of free radical reaction-initiating species per mole of free radical initiator; thus, the concentration of the free radical initiator can be stated in terms which describe the number of free radical reaction-initiating species generated per mole of free radical initiator. The term "equivalent" is often used to describe the number of reaction-initiating species produced per mole of free radical initiator. For example, one skilled in the art will readily recognize that di-t-butylperoxide can generate two free radical reaction-initiating species per mole of di-t-butylperoxide, while 2,5-bis(t-butylperoxy)-2,5-dimethylhexane can generate four free radical reaction-initiating species per mole of 2,5-bis(t-butylperoxy)-2,5-dimethylhexane.

In an aspect, the thiol compound can be formed in the absence of a solvent. However, in other aspects, the thiol compound can be formed in the presence of a solvent. Typically, when used, the solvent can be present in an amount up to about 1,000 wt. %, based on the weight of the olefin compound. Alternatively, the formation of the thiol compound can be performed in the presence of a solvent in an amount up to about 750 wt. %, up to about 500 wt. %, up to about 250 wt. %, up to about 200 wt. %, up to about 150 wt. %, or up to about 100 wt. %. When a solvent is utilized, the minimum amount of solvent utilized can be at least about 5 wt. %, at least about 10 wt. %, at least about 25 wt. %, at least about 50 wt. %, or at least about 75 wt. %, based on the weight of the olefin compound. Generally, the range of solvent which can be utilized can range from any minimum amount of solvent disclosed herein to any maximum amount of solvent disclosed herein. In some non-limiting aspects, the formation of the thiol compound can be performed in the presence of a solvent in an amount of from about 5 wt. % to about 1,000 wt. %, from about 10 wt. % to about 750 wt. %, from about 25 wt. % to about 500 wt. %, from about 50 wt. % to about 250 wt. %, from about 50 wt. % to about 150 wt. %, or from about 75 wt. % to about 125 wt. %, based on the weight of the olefin compound. The solvent can be contacted with the olefin compound, $H_2S$, diphenylamine and/or the phenol compound, and the photoinitiator and/or free radical initiator in step 1 of the process, and remain present during the formation of the thiol compound. Alternatively, the solvent can be added after the initial contacting in step 1. Solvents which can be utilized as the solvent are described herein, and these solvents can be utilized without limitation in the processes described herein.

In the processes for producing a thiol compound disclosed herein, it is contemplated that at least about 60% of the carbon-carbon double bonds of the olefin compound can react to form a thiol group. Often, at least about 65% of the carbon-carbon double bonds of the olefin compound can react to form a thiol group; alternatively, at least about 70%; alternatively; at least about 75%; alternatively, at least about 80%; alternatively, at least about 85%; alternatively, at least about 90%; alternatively, at least about 95%; alternatively, at least about 98%; or alternatively, at least about 99%.

Likewise, in the processes for producing a thiol compound disclosed herein, the percent conversion typically can be at least about 70%. More often, the percent conversion can be at least about 75%; alternatively, at least about 85%; alternatively, at least about 90%; alternatively, at least about 92%; alternatively, at least about 95%; alternatively, at least about 98%; or alternatively, at least about 99%. The percent conversion is based on the conversion of carbon-carbon double bonds of the olefin compound to a sulfur-containing group (e.g., a thiol group or a sulfide group).

Unexpectedly, the percent conversion of the olefin compound in the process for producing the thiol compound can be greater than the percent conversion obtained by conducting the process without diphenylamine and/or a phenol compound, under the same reaction conditions. Often, the percent conversion can be at least about 2% greater than that obtained by conducting the process without diphenylamine and/or the phenol compound, under the same reaction conditions; alternatively, at least about 5% greater; alternatively, at least about 8% greater; alternatively, at least about 10% greater; alternatively, at least about 12% greater; or alternatively, at least about 15% greater, and often up to 20-40% greater in some aspects. The percent conversion is based on the conversion of carbon-carbon double bonds of the olefin compound to a sulfur-containing group (e.g., a thiol group or a sulfide group).

Also unexpectedly, the time required to reach a target percent conversion of the olefin compound in the process for producing the thiol compound can be less than the time required to reach the target percent conversion obtained by conducting the process without diphenylamine and/or the phenol compound, under the same reaction conditions. Often, the time required to reach the target conversion can be at least about 2% less than that obtained by conducting the process without diphenylamine and/or the phenol compound, under the same reaction conditions; alternatively, at least about 5% less; alternatively, at least about 10% less; alternatively, at least about 15% less; alternatively, at least about 20% less; or alternatively, at least about 25% less, and often up to 50-75% less in some aspects.

Once formed, the thiol compound, or specific fractions of the crude reaction product containing the thiol compound, can be purified and/or isolated and/or separated using suitable techniques which include, but are not limited to, evaporation, distillation, crystallization, extraction, washing, decanting, filtering, drying, including combinations of more than one of these techniques. In one aspect, the process for producing a thiol compound can further comprise a step of separating or removing at least a portion of the $H_2S$, of the diphenylamine and/or the phenol compound, of the photoinitiator and/or free radical initiator, of the olefin compound, or any combination thereof, from the thiol compound. For instance, these materials can be separated or removed by distillation, by short path distillation, by wiped film evaporation, or by a combination of these techniques.

Processes for Producing Sulfide Compounds

Aspects of this invention also are directed to processes for forming a sulfide compound (a compound with at least one —S— group). Such processes can comprise, consist essentially of, or consist of (I) contacting (A) an olefin compound, (B) a mercaptan compound, and (C) diphenylamine and/or a phenol compound; and (II) forming the sulfide compound. Generally, the features of the process (e.g., the olefin compound, the mercaptan compound, the mercaptan to carbon-carbon double bond ratio, the amount of diphenylamine and/or the phenol compound, and the conditions under which the sulfide compound is formed, among others) are independently described herein and these features can be combined in any combination to further describe the disclosed process. Sulfide compounds produced by any of these processes also are encompassed herein.

In some aspects, the contacting step (step (I) of the process) can include contacting the olefin compound, the mercaptan compound, and diphenylamine and/or a phenol compound, as well as additional unrecited materials (e.g., a photoinitiator, a free radical initiator, a solvent, etc.). In other aspects, the contacting step can consist essentially of contacting the olefin compound, the mercaptan compound, and diphenylamine and/or the phenol compound or, alternatively, can consist of contacting the olefin compound, the mercaptan compound, and diphenylamine and/or the phenol compound. Likewise, additional materials or features can be employed in the forming step (step II of the process). For instance, the formation of the sulfide compound can occur in the presence of ultraviolet light, as discussed herein. Moreover, it is contemplated that the processes for producing a sulfide compound can employ more than one olefin compound and/or more than one mercaptan compound. Additionally or alternatively, the processes for forming a sulfide compound can employ two or more phenol compounds, or diphenylamine in combination with a phenol compound.

If utilized in the process for producing a sulfide compound, the amounts of the photoinitiator and/or free radical initiator and/or solvent are not limited to any particular range or amount, and can be present in any of the amounts and ranges of amounts disclosed hereinabove in regards to the processes for producing thiol compounds. For instance, the amount of the photoinitiator and/or free radical initiator, independently, can be in a range from about 0.05 wt. % to about 5 wt. %, from about 0.1 wt. % to about 2 wt. %, from about 0.1 wt. % to about 1 wt. %, from about 0.2 wt. % to about 1 wt. %, or from about 0.2 wt. % to about 0.8 wt. %, based on the weight of the olefin compound.

In the processes disclosed herein, the molar ratio of SH of the mercaptan compound to carbon-carbon double bonds of the olefin compound is not limited to any particular range. In some aspects, however, the molar ratio can be in a range from about 10:1 to about 1:10, or from about 5:1 to about 1:5, or from about 4:1 to about 1:4. Other suitable ranges for the molar ratio of SH of the mercaptan compound to carbon-carbon double bonds of the olefin compound can include, but are not limited to, from about 3:1 to about 1:3, or from about 2:1 to about 1:2, or from about 1.5:1 to about 1:1.5, or from about 1.3:1 to about 1:1.3, or from about 1.2:1 to about 1:1.2, or from about 1.1:1 to about 1:1.1. For example, the molar ratio of SH of the mercaptan compound to carbon-carbon double bonds of the olefin compound can be in a range from about 1:1.05 to about 1:1.2, such that there is a molar excess of the olefin compound.

Generally, the amount of diphenylamine and/or the phenol compound utilized in the process for producing a sulfide compound is not particularly limited. However, in one aspect, the amount of diphenylamine and/or the phenol compound, based on the weight of the olefin compound, can be in a range from about 0.05 wt. % to about 5 wt. %, from about 0.05 wt. % to about 3 wt. %, or from about 0.05 wt. % to about 1 wt. %. In another aspect, the amount of diphenylamine and/or the phenol compound can be in a range from about 0.1 wt. % to about 4 wt. %, from about 0.1 wt. % to about 2 wt. %, from about 0.1 wt. % to about 1 wt. %, or from about 0.2 wt. % to about 0.5 wt. %. In yet another aspect, the amount of diphenylamine and/or the phenol compound can be in a range from about 0.25 wt. % to about 2 wt. %, from about 0.25 wt. % to about 1.5 wt. %, from about 0.25 wt. % to about 1 wt. %, or from about 0.5 wt. % to about 1 wt. %.

Steps I and II of the process for producing a sulfide compound independently can be conducted at a variety of temperatures, pressures, and time periods, and these temperatures, pressures, and time periods can typically fall within the respective ranges of temperatures, pressures, and time periods disclosed hereinabove in relation to the process for producing a thiol compound.

Moreover, and similar to the process for producing a thiol compound, the sulfide compound in the process for producing the sulfide compound can be formed in the presence of electromagnetic radiation. For instance, the sulfide compound can be formed in the presence of ultraviolet light. Additionally or alternatively, the sulfide compound can be formed by light photolysis initiation of a free radical initiator. Additionally or alternatively, the sulfide compound can be formed under conditions suitable for the thermal decomposition of a free radical initiator. Additionally, a photoinitiator can be utilized in conjunction with ultraviolet light or light photolysis initiation of a free radical initiator. Free radicals, therefore, can be generated in situ by a suitable energy source, or can be generated by the thermal decomposition of a free radical initiator, or by a combination of these sources. The sulfide compound can be formed in the presence of free radicals from any one of aforementioned sources, including combinations thereof, but is not limited to free radicals generated only by these means. When the electromagnetic radiation is ultraviolet light, ultraviolet light in the range, for example, from about 172 to about 450 nm, from about 185 to about 380 nm, from about 200 to about 350 nm, or from about 245 to about 300 nm, can be employed. Ultraviolet light can be supplied from ultraviolet lamps, but other sources of ultraviolet light can be employed, and are to be considered within the scope of the present invention.

In the processes for producing a sulfide compound disclosed herein, it is contemplated that at least about 60% of the carbon-carbon double bonds of the olefin compound can react to form a sulfide group. Often, at least about 65% of the carbon-carbon double bonds of the olefin compound can react to form a sulfide group; alternatively, at least about 70%; alternatively; at least about 75%; alternatively, at least about 80%; alternatively, at least about 85%; alternatively, at least about 90%; alternatively, at least about 95%; alternatively, at least about 98%; or alternatively, at least about 99%.

Likewise, in the processes for producing a sulfide compound disclosed herein, the percent conversion typically can be at least about 70%. More often, the percent conversion can be at least about 75%; alternatively, at least about 85%; alternatively, at least about 90%; alternatively, at least about 92%; alternatively, at least about 95%; alternatively, at least about 98%; or alternatively, at least about 99%. The percent conversion is based on the conversion of carbon-carbon double bonds of the olefin compound to a sulfur-containing group (e.g., a thiol group or a sulfide group).

Unexpectedly, the percent conversion of the olefin compound in the process for producing the sulfide compound can be greater than the percent conversion obtained by conducting the process without diphenylamine and/or a phenol compound, under the same reaction conditions. Often, the percent conversion can be at least about 2% greater than that obtained by conducting the process without diphenylamine and/or the phenol compound, under the same reaction conditions; alternatively, at least about 5% greater; alternatively, at least about 8% greater; alternatively, at least about 10% greater; alternatively, at least about 12% greater; or alternatively, at least about 15% greater, and often up to 20-40% greater in some aspects. The percent conversion is based on the conversion of carbon-carbon double bonds of the olefin compound to a sulfur-containing group (e.g., a thiol group or a sulfide group).

Also unexpectedly, the time required to reach a target percent conversion of the olefin compound in the process for producing the sulfide compound can be less than the time required to reach the target percent conversion obtained by conducting the process without diphenylamine and/or a phenol compound, under the same reaction conditions. Often, the time required to reach the target percent conversion can be at least about 2% less than that obtained by conducting the process without diphenylamine and/or the phenol compound, under the same reaction conditions;

alternatively, at least about 5% less; alternatively, at least about 10% less; alternatively, at least about 15% less; alternatively, at least about 20% less; or alternatively, at least about 25% less, and often up to 50-75% less in some aspects Once formed, the sulfide compound, or specific fractions of the crude reaction product containing the sulfide compound, can be purified and/or isolated and/or separated using suitable techniques which include, but are not limited to, evaporation, distillation, crystallization, extraction, washing, decanting, filtering, drying, including combinations of more than one of these techniques. In one aspect, the process for producing a sulfide compound can further comprise a step of separating or removing at least a portion of the diphenylamine and/or the phenol compound, of the photoinitiator and/or free radical initiator (if used), of the olefin compound, of the mercaptan compound, or any combination thereof, from the sulfide compound. For instance, these materials can be separated or removed by distillation, by short path distillation, by wiped film evaporation, or by a combination of these techniques.

Exemplary sulfide compounds that can be produced via the processes disclosed herein can include, for instance, symmetrical sulfides, such as diethyl sulfide, dipropryl sulfide, dibutyl sulfide, dipentyl sulfide, dihexyl sulfide, diheptyl sulfide, dioctyl sulfide, dinonyl sulfide, didecyl sulfide, didodecyl sulfide, and the like, as well as related non-symmetrical sulfides.

Olefin Compounds

The olefin compound can be a compound having at least one carbon-carbon double bond that can be converted to a thiol compound and/or a sulfide compound utilizing a process described herein. Generally, the olefin compound can have any combination of the features for the compound having at least one carbon-carbon double bond described herein.

In an aspect, the olefin compound used in the process can have at least 2 carbon atoms, at least 3 carbon atoms, at least 4 carbon atoms, or at least 5 carbon atoms. In some aspects, the olefin compound used in the process can have a maximum of 100 carbon atoms, 80 carbon atoms, 60 carbon atoms, 50 carbon atoms, 40 carbon atoms, 30 carbon atoms, 25 carbon atoms, 20 carbon atoms, 15 carbon atoms, or 10 carbon atoms. Generally, the olefin compound used in the process can have from any minimum number of carbon atoms described herein to any maximum number of carbon atoms described herein. For example, in some non-limiting aspects, the olefin compound can have from 2 to 100 carbon atoms, from 3 to 80 carbon atoms, from 4 to 60 carbon atoms, or from 5 to 60 carbon atoms. Other carbon atom number ranges can be readily envisioned from the present disclosure and are encompassed herein.

In an aspect, the olefin compound can be a hydrocarbon compound, a heteroatomic compound, or any combination thereof; alternatively, a hydrocarbon compound; or alternatively, a heteroatomic compound. In some aspects, the olefin compound can be aliphatic, aromatic, or any combination thereof; alternatively, aliphatic; or alternatively, aromatic. In other aspects, the olefin compound can be acyclic, cyclic, or any combination thereof; alternatively, acyclic; or alternatively, cyclic.

The olefin compound used in these processes has at least one carbon-carbon double bond. In one aspect, the olefin compound has from 1 to 10 double bonds; alternatively, from 1 to 8 double bonds; alternatively, from 3 to 5 double bonds; or alternatively, from 2 to 4 double bonds. In another aspect, the olefin compound has only one carbon-carbon double bond; alternatively, only two double bonds; alternatively, only three double bonds; alternatively, only four double bonds; alternatively, only five double bonds; or alternatively, only six double bonds.

Representative and non-limiting examples of olefin compounds having only one carbon-carbon double bond can comprise, consist essentially of, or consist of, either singly or in any combination, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, 1-undecene, 1-dodecene, 1-tridecene, 1-tetradecene, 1-pentadecene, or styrene.

Representative and non-limiting examples of cyclic olefin compounds having only one carbon-carbon double bond can comprise, consist essentially of, or consist of, either singly or in any combination, cyclopentene, cyclohexene, cycloheptene, or cyclooctene. In some aspects, cyclic olefin compounds having only one carbon-carbon double bond can comprise, consist essentially of, or consist of, cyclopentene; alternatively, cyclohexene; alternatively, cycloheptene; or alternatively, cyclooctene.

Suitable examples of compounds having at least two carbon-carbon double bonds that may be employed in the processes disclosed herein can comprise, consist essentially of, or consist of, either singly or in any combination, butadiene, isoprene, cyclobutadiene, cyclopentadiene, cyclohexadiene, cyclooctadiene, norbornadiene, vinylcyclohexene, vinylnorbornene, divinylbenzene, or cyclopentadiene dimer. Hence, mixtures or combinations of more than one compound having at least two double bonds can be employed. Accordingly, the compound having at least two double bonds can comprise, consist essentially of, or consist of, either singly or in any combination, butadiene, isoprene, cyclobutadiene, cyclopentadiene, cyclohexadiene, or cyclooctadiene; alternatively, norbornadiene, vinylcyclohexene, vinylnorbornene, or divinylbenzene; alternatively, butadiene; alternatively, isoprene; alternatively, cyclobutadiene; alternatively, cyclopentadiene; alternatively, cyclohexadiene; alternatively, cyclooctadiene; alternatively, norbornadiene; alternatively, vinylcyclohexene; alternatively, vinylnorbornene; alternatively, divinylbenzene; or alternatively, cyclopentadiene dimer.

In an aspect, the olefin compound can comprise, consist essentially of, or consist of, one or more compounds having only three carbon-carbon double bonds. Illustrative non-limiting examples of such compounds can comprise, consist essentially of, or consist of, singly or in any combination, trivinylcyclohexane, trivinylbenzene, cycloheptatriene, dimethyl heptatriene, octatriene, cyclooctatriene, or cyclododecatriene. In one aspect, the compound having only three double bonds can comprise, consist essentially of, or consist of, trivinylcyclohexane. In another aspect, the compound having only three double bonds can comprise, consist essentially of, or consist of, trivinylbenzene. In another aspect, the compound can comprise, consist essentially of, or consist of, cycloheptatriene. In another aspect, the compound having only three double bonds can comprise, consist essentially of, or consist of, dimethyl heptatriene. In another aspect, the compound having only three double bonds can comprise, consist essentially of, or consist of, octatriene. Yet, in another aspect, the compound having only three double bonds can comprise, consist essentially of, or consist of, cyclooctatriene. In still another aspect, the compound having only three double bonds can comprise, consist essentially of, or consist of, cyclododecatriene.

Compounds having four or more carbon-carbon bonds also are contemplated. For instance, the compound having four or more carbon-carbon bonds can comprise, consist essentially of, or consist of, cyclooctatetraene; alternatively, cyclododecatetraene; alternatively, a polybutadiene; or alternatively, a combination of two or more of these compounds.

Additionally, olefin metathesis products having two or more carbon-carbon double bonds can be utilized. As such, the compound having two or more double bonds can comprise, consist essentially of, or consist of, either singly or in any combination, an olefin metathesis product of one or more of vinylcyclohexene, vinylnorbornene, divinylbenzene, trivinylcyclohexane, trivinylbenzene, norbornene, norbornadiene, cyclooctadiene, trivinylcyclohexane, and cyclododecatriene. For instance, the compound having two or more carbon-carbon double bonds can comprise, consist essentially of, or consist of, an olefin metathesis product of vinylcyclohexene, an olefin metathesis product of vinylcyclohexene with vinylnorbornene, and so forth.

In an aspect, the olefin compound can comprise, consist essentially of, or consist of, a terpene compound having at least two carbon-carbon double bonds. For example, the compound having two or more double bonds can comprise, consist essentially of, or consist of, either singly or in any combination, a monoterpene, a sesquiterpene, a diterpene, a sesterpene, or a triterpene. Accordingly, the compound can comprise, consist essentially of, or consist of, a monoterpene or a sesquiterpene; alternatively, a monoterpene; alternatively, a sesquiterpene; alternatively, a diterpene; alternatively, a sesterpene; or alternatively, a triterpene. The hydrocarbon terpene can comprise, consist essentially of, or consist of, a cyclic terpene in some aspects of this invention, while in other aspects, the hydrocarbon terpene can comprise, consist essentially of, or consist of, an acyclic terpene.

The olefin compound can comprise, consist essentially of, or consist of, either singly or in any combination, myrcene, ocimene (i.e., (E)-ocimene, (Z)-ocimene, or mixtures thereof), alloocimene, cosmene, limonene, terpinolene, terpinene (i.e., α-terpinene, γ-terpinene, or mixtures thereof), pinene (i.e., α-pinene, β-pinene, or mixtures thereof), phellandrene (i.e., α-phellandrene, β-phellandrene, or mixtures thereof), or 1,3,8-para-menthatriene; alternatively, myrcene; alternatively, ocimene; alternatively, alloocimene; alternatively, cosmene; alternatively, limonene (e.g., D-limonene); alternatively, terpinolene, alternatively, terpinene; alternatively, pinene; alternatively, phellandrene; or alternatively, 1,3,8-para-menthatriene. Yet, in other aspects, the compound can comprise, consist essentially of, or consist of, either singly or in any combination, farnesene (i.e., (E)-α-farnesene, (Z)-α-farnesene, (E)-β-farnesene, (Z)-β-farnesene, or mixtures thereof), bisabolene (i.e., α-bisabolene, β-bisabolene, or mixtures thereof), zingiberene, β-curcumene, laurene, elemene (i.e., α-elemene, β-elemene, or mixtures thereof), humulene, germacrene, cadinene (i.e., α-cadinene, β-cadinene, γ-cadinene, or mixtures thereof), selinene (i.e., α-selinene, β-selinene, or mixtures thereof), eremophilene, nootkatene, or valencene; alternatively, farnesene; alternatively, bisabolene; alternatively, zingiberene; alternatively, β-curcumene; alternatively, laurene; alternatively, elemene; alternatively, humulene; alternatively, germacrene; alternatively, cadinene; alternatively, selinene; alternatively, eremophilene; alternatively, nootkatene; or alternatively, valencene.

In accordance with another aspect, the olefin compound can comprise, consist essentially of, or consist of, either singly or in any combination, cembrene, abietadiene, casbene, haslene, or squalene. Thus, each of these materials can be employed singularly; for example, the compound can comprise, consist essentially of, or consist of, haslene; alternatively, the compound having two or more double bonds can comprise, consist essentially of, or consist of, squalene.

In some aspects, the olefin compound can comprise, consist essentially of, or consist of, an unsaturated triglyceride, while in other aspects, the olefin compound can comprise, consist essentially of, or consist of, an unsaturated natural source oil. Thus, thiol compounds with functional groups, such as esters, can be formed (e.g., thiol esters) using the processes of this invention. In an aspect, the olefin compound can comprise, consist essentially of, or consist of, either singly or in any combination, soybean oil, corn oil, castor bean oil, or canola oil. Such materials are disclosed, for instance, in U.S. Pat. No. 7,989,655, the disclosure of which is incorporated herein by reference in its entirety.

In yet another aspect, the olefin compound can comprise, consist essentially of, or consist of, either singly or in any combination, any of the following structures:

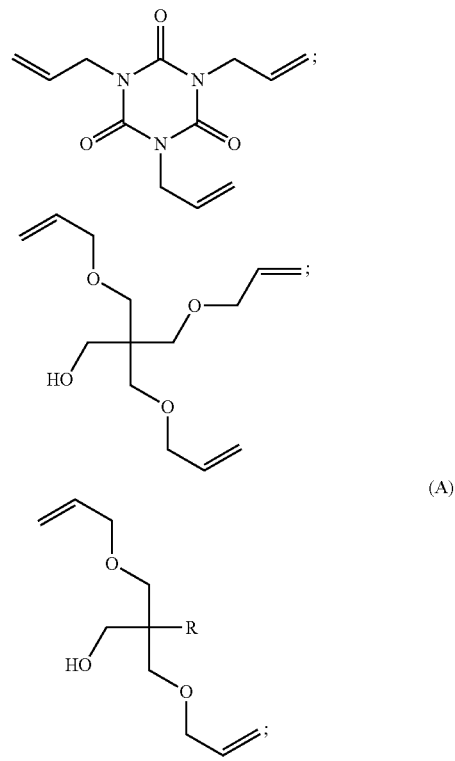

(A)

wherein R in formula (A) is a $C_1$-$C_{18}$ hydrocarbyl group. R can be a $C_1$ to $C_{18}$ alkyl group, a $C_4$ to $C_{18}$ cycloalkyl group, a $C_6$ to $C_{18}$ aryl group, or a $C_7$ to $C_{18}$ aralkyl group; alternatively, R can be a $C_1$ to $C_5$ alkyl group, a $C_5$ to $C_8$ cycloalkyl group, a $C_6$ to $C_8$ aryl group, or a $C_7$ to $C_8$ aralkyl group. Accordingly, in one aspect, R can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group.

Mercaptan Compounds

A mercaptan compound is a compound having at least one —SH group. Generally, the mercaptan compound can be any mercaptan compound which can be converted to a sulfide compound utilizing a process described herein. Generally, the mercaptan compound can have any combination of the features for the mercaptan compound described herein. The mercaptan compound used in these processes has at least one SH group. In one aspect, the mercaptan compound can have from 1 to 10 SH groups; alternatively, from 2 to 8 SH groups; alternatively, from 2 to 6 SH groups; or alternatively, from 1 to 4 SH groups. In another aspect, the mercaptan compound has only one SH group; alternatively, only two SH groups; alternatively, only three SH groups; alternatively, only four SH groups; alternatively, only five SH groups; or alternatively, only six SH groups.

In an aspect, the mercaptan compound used in the process can have at least 1 carbon atom, at least 2 carbon atoms, at least 3 carbon atoms, at least 4 carbon atoms, or at least 5 carbon atoms. In some aspects, the mercaptan compound used in the process can have a maximum of 100 carbon atoms, 80 carbon atoms, 60 carbon atoms, 50 carbon atoms, 40 carbon atoms, 30 carbon atoms, 25 carbon atoms, 20 carbon atoms, 15 carbon atoms, or 10 carbon atoms. Generally, the mercaptan compound used in the process can have from any minimum number of carbon atoms described herein to any maximum number of carbon atoms described herein. For example, in some non-limiting aspects, the mercaptan compound can have from 1 to 100 carbon atoms, from 2 to 80 carbon atoms, from 1 to 60 carbon atoms, or from 2 to 60 carbon atoms. Other carbon atom number ranges can be readily envisioned from the present disclosure and are encompassed herein.

In an aspect, the mercaptan compound can have the formula R—SH, the formula HS—R—SH, the formula HO—R—SH, or any combination thereof; alternatively R—SH; alternatively, HS—R—SH; or alternatively, HO—R—SH. In some aspects, R can be a $C_1$-$C_{18}$ hydrocarbon group; alternatively, a $C_1$-$C_{10}$ hydrocarbon group; alternatively, a $C_1$-$C_5$ hydrocarbon group; alternatively, a $C_1$-$C_{18}$ alkane group; alternatively, a $C_1$-$C_{10}$ alkane group; alternatively, a $C_1$-$C_5$ alkane group; alternatively, a $C_1$-$C_{18}$ n-alkane group; alternatively, a $C_1$-$C_{10}$ n-alkane group; alternatively, a $C_1$-$C_5$ n-alkane group; alternatively, a $C_6$-$C_{18}$ arene group; alternatively, a $C_6$-$C_{10}$ arene group; alternatively, a $C_7$-$C_{18}$ alkylarene/arylalkane group; or alternatively, a $C_6$-$C_{10}$ alkylarene/arylalkane group. Accordingly, R can be a methane group, an ethane group, a propane group, a butane group, a pentane group, a hexane group, a heptane group, an octane group, a nonane group, or a decane group; alternatively, R can be a methane group, an ethane group, a propane group, a butane group, or a pentane group; alternatively, R can be a methane group; alternatively, R can be an ethane group; alternatively, R can be a propane group; alternatively, R can be a butane group; alternatively, R can be a pentane group; alternatively, R can be a hexane group; alternatively, R can be a heptane group; alternatively, R can be an octane group; alternatively, R can be a nonane group; or alternatively, R can be a decane group. In some aspects, R can be a benzene group, a toluene group, a xylene group, or a naphthylene group; alternatively, a benzene group, a toluene group, or a xylene group; alternatively, a benzene group; alternatively, a toluene group; alternatively, a xylene group; or alternatively, a naphthylene group. In some aspects, R can be a phenylalkane group or a naphthylalkane group; alternatively, a phenylalkane group; or alternatively, a naphthylalkane group. In further aspects, R can be a phenylmethane group.

In accordance with an aspect of this invention, the mercaptan compound can comprise, consist essentially of, or consist of, an alkyl mercaptan, for instance, an n-alkyl mercaptan. In accordance with another aspect of this invention, the mercaptan compound can comprise, consist essentially of, or consist of, methyl mercaptan, ethyl mercaptan, n-propyl mercaptan, n-butyl mercaptan, t-butyl mercaptan, n-pentyl mercaptan, phenyl mercaptan, or combinations thereof. Yet, in accordance with another aspect of this invention, the mercaptan compound can comprise, consist essentially of, or consist of, methyl mercaptan; alternatively, ethyl mercaptan; alternatively, n-propyl mercaptan; alternatively, n-butyl mercaptan; alternatively, t-butyl mercaptan; alternatively, n-pentyl mercaptan; or alternatively, phenyl mercaptan.

In some aspects, the mercaptan compound can comprise, consist essentially of, or consist of, mercaptomethanol, 2-mercaptoethanol, 3-mercaptopropanol, 4-mercaptobutanol, 5-mercaptopentanol, 6-mercaptohexanol, or combinations thereof. In other aspects, the mercaptan compound can comprise, consist essentially of, or consist of, mercaptomethanol; alternatively, 2-mercaptoethanol; alternatively, 3-mercaptopropanol; alternatively, 4-mercaptobutanol; alternatively, 5-mercaptopentanol; or alternatively, 6-mercaptohexanol. In yet another aspect, the mercaptan compound can comprise, consist essentially of, or consist of, 1,2-dithiolethane.

Solvents

As described above, the thiol compounds and sulfide compounds can be formed in the presence of a solvent. The solvent can comprise, consist essentially of, or consist of, a hydrocarbon, an aromatic hydrocarbon, a ketone, an alcohol, an ether, or combinations thereof. Hence, mixtures and/or combinations of solvents can be utilized in the processes of forming thiol compounds or sulfide compounds disclosed herein.

In an aspect, the solvent employed in forming the thiol compound or sulfide compound can comprise, consist essentially of, or consist of, a hydrocarbon solvent. Suitable hydrocarbon solvents can include, for example, aliphatic hydrocarbons, petroleum distillates, or combinations thereof. Aliphatic hydrocarbons which can be useful as the solvent include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons can be cyclic or acyclic, and/or can be linear or branched, unless otherwise specified.

Non-limiting examples of suitable acyclic aliphatic hydrocarbon solvents that can be utilized singly or in any combination include pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), decane (n-decane or a mixture of linear and branched $C_{10}$ acyclic aliphatic hydrocarbons), and combinations thereof; alternatively, pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof alternatively, hexane (n-hexane or a mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons).

In an aspect, the solvent employed in forming the thiol compound or sulfide compound can comprise, consist essentially of, or consist of, an aromatic hydrocarbon solvent. Aromatic hydrocarbons can include $C_6$ to $C_{30}$ aromatic hydrocarbons; alternatively, $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

In an aspect, the solvent employed in forming the thiol compound or sulfide compound can comprise, consist essentially of, or consist of, a ketone solvent, an alcohol solvent, an ether solvent, or combinations thereof alternatively, a ketone solvent; alternatively, an alcohol solvent; or alternatively, an ether solvent. Suitable ketones, alcohols, or ethers include $C_2$ to $C_{20}$ ketones, alcohols, or ethers; alternatively, $C_2$ to $C_{10}$ ketones, alcohols, or ethers; or alternatively, $C_2$ to $C_5$ ketones, alcohols, or ethers. Non-limiting examples of suitable ketone solvents can include acetone, ethyl methyl ketone, and combinations thereof. Non-limiting examples of suitable alcohol solvents can include methanol, ethanol, propanol, isopropanol, n-butanol, isobutanol, pentanol, hexanol, heptanol, octanol, benzyl alcohol, phenol, cyclohexanol, or combinations thereof. Suitable ether solvents can be cyclic or acyclic, non-limiting examples of which can include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an aspect, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group.

Articles

Formulations, compositions, and various articles of manufacture can contain the thiol or sulfide compounds disclosed herein. Such formulations, compositions, and articles of manufacture are encompassed herein, and can include coating and adhesive products.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

Thiol compounds were produced in accordance with the following procedure. A 1.5-L ultraviolet light reactor was used for each example; the working volume was 1.2 L. The 1.5-L stainless-steel reactor had a 100-watt quartz lamp well that was mounted horizontal to an off-set stir shaft. The reactor was equipped with a thermowell, cooling coils, a charge port, a sample port, and a bottom drain valve. To the reactor, 1-dodecene (300 g), the desired amount of the additive (e.g., diphenylamine, the phenol compound, etc.), free radical initiator (if utilized), photoinitiator (if utilized), and solvent (if utilized) were charged to the reactor through the charge port. The reactor was sealed and pressure checked with nitrogen at 450 psig (3103 kPag). The reactor was vented and $H_2S$ (600 g; 10:1 molar ratio of $H_2S$:dodecene) was charged to the reactor; the operating pressure was generally between 235 and 400 psig (1620-2758 kPag). During the experiments, the 100-watt UV lamp operated at 1.1-1.5 amps and 28-103 volts. The temperature of the reactor contents was controlled by setting the external circulating bath at the desired temperature of approximately 25° C. Raman spectroscopy was used to monitor olefin consumption according to the strength of the olefin peak at 1640 $cm^{-1}$.

Examples 1-3

Reactions of Hydrogen Sulfide with 1-dodecene Without Diphenylamine or a Phenol Compound Example 1 utilized the general experimental procedure described above, and was conducted as a series of 6 duplicate reactions. The average reaction time and molar percent olefin conversion of this series are reported below in Table I. Examples 2-3 also utilize the general experimental procedure described above, using triethylphosphite (TEP, weight percentage based on the amount of 1-dodecene) and Irgacure® 500 as additives in the specified amounts. Reaction times and molar olefin conversion are reported for Examples 2-3 in Table I.

TABLE I

| Examples 1-3. | | | | | | |
|---|---|---|---|---|---|---|
| Example | Additive | Additive (wt. %) | Irgacure ® 500 (g) | Solvent (mL) | Percent Conversion | Time (min) |
| 1 | — | — | — | 0 | 92 | 57 |
| 2 | TEP | 0.25 | 1 | 0 | 99 | 11 |
| 3 | TEP | 0.08 | 1 | 0 | 99 | 11 |

Examples 4-16

Reactions of Hydrogen Sulfide with 1-dodecene (or Limonene) with Amine Additives Examples 4-12 and 14-16 utilized the general experimental procedure described above, and were conducted as single, individual experiments. Example 13 followed the general procedure described above, except limonene (15:1 molar ratio of $H_2S$ to double bonds of limonene) was used in place of 1-dodecene. The amount of amine additive (weight percentage based on the weight of 1-dodecene or limonene), THF solvent (where used), and resulting molar percent olefin conversions after the respective reaction times are listed in Table II. The aromatic amines of Examples 4 and 5 (1,2,3,4-tetrahydroisoquioline (THQ) and para-toluidine, respectively) each slowed the thiolation reaction. In contrast, and surprisingly, certain examples (e.g., Examples 7-10 and 12-13) conducted in the presence of diphenylamine (DPA) demonstrated percent conversions similar to that of Examples 2-3 (which used TEP), and much shorter reaction times than Example 1. These results are illustrated graphically in FIG. 1 for Examples 1 and 3 and Examples 6 and 8.

Example 7 demonstrates that only 33 minutes were required to reach a high molar olefin conversion of 97%, whereas for Example 1, 57 minutes (nearly double the reaction time) were required to reach a lower molar olefin conversion of 92%. The unexpected catalytic effect of diphenylamine was even more surprising in light of the performance of the alkylated diphenylamines AO130 (nonylated) from King Industries and L57 (octylated/butylated) from BASF of Examples 14-16, which could not duplicate the high molar olefin conversions of 95-97% achieved in certain diphenylamine examples, even with longer reaction times. Instead, the alkylated diphenylamines of Examples 14-16 demonstrated an inhibitory effect on the thiolation reaction, as can be seen by comparison with Example 1.

Moreover, as shown by comparing Example 6 with the other diphenylamine examples, the use of diphenylamine with a photoinitiator appeared to result in a synergistic improvement in olefin conversion rate.

TABLE II

Examples 4-16.

| Example | Additive | Additive (wt. %) | Irgacure ® 500 (g) | THF (mL) | Percent Conversion | Time (min) |
|---|---|---|---|---|---|---|
| 4 | THQ | 0.5 | 0 | 0 | 76 | 132 |
| 5 | p-toluidine | 0.33 | 0.33 | 0 | 74 | 57 |
| 6 | DPA | 0.5 | 0 | 10 | 87 | 61 |
| 7 | DPA | 0.5 | 1 | 0 | 97 | 33 |
| 8 | DPA | 0.5 | 1 | 0 | 97 | 41 |
| 9 | DPA | 0.5 | 1 | 0 | 96 | 41 |
| 10 | DPA | 0.25 | 0.5 | 0 | 95 | 43 |
| 11 | DPA | 0.08 | 0.5 | 0 | 71 | 95 |
| 12 | DPA | 1.0 | 1 | 0 | 97 | 35 |
| 13 | DPA | 0.55 | 0.5 | 0 | 98 | 35 |
| 14 | AO130 | 0.5 | 1 | 0 | 89 | 97 |
| 15 | AO130 | 1 | 1 | 0 | 48 | 60 |
| 16 | L57 | 1 | 1 | 0 | 94 | 119 |

Examples 17-24

Reactions of Hydrogen Sulfide with 1-dodecene with a Phenol Additive

Examples 17-24 utilized the general experimental procedure described above, and were conducted as single, individual experiments. The amount of phenol additive (weight percentage based on the weight of 1-dodecene), acetone solvent (where used), and resulting molar olefin conversion after the respective reaction times are listed in Table III. Surprisingly, certain reactions conducted in the presence of a phenol compound demonstrated an even higher olefin conversion rate than analogous reactions using diphenylamine. For instance, each of Examples 7-9 (diphenylamine) and Example 18 (BHT) had similar olefin conversions, and comparable to that of Examples 2-3 (TEP); however, the reaction occurred much more quickly in the presence of BHT, needing only 21 minutes of reaction time, as compared to 33-41 minutes when using diphenylamine. Additionally, the olefin conversion rates of thiolation reactions with BHT approached the conversion rates achieved using the phosphite additives of Examples 2-3. Moreover, carvacrol, 2,2'-ethylidene-bis(4,6-di-tert-butylphenol) (1290), and pentaerythritol tetrakis(3,5-di-tert-butyl-4-hydroxyhydrocinnamate) (Irganox® 1010) each unexpectedly demonstrated molar olefin conversions and reaction times comparable to those of diphenylamine and far superior to Example 1.

TABLE III

Examples 17-24.

| Example | Additive | Additive (wt. %) | Irgacure ® 500 (g) | Acetone (mL) | Percent Conversion | Time (min) |
|---|---|---|---|---|---|---|
| 17 | BHT | 0.5 | 1.5 | 0 | 95 | 27 |
| 18 | BHT | 0.5 | 1 | 0 | 97 | 21 |
| 19 | BHT | 0.33 | 0.5 | 0 | 97 | 24 |
| 20 | BHT | 0.5 | 0.25 | 0 | 93 | 27 |
| 21 | BHT | 0.5 | 0 | 50 | 92 | 45 |
| 22 | carvacrol | 0.5 | 1 | 0 | 96 | 39 |
| 23 | 1290 | 0.5 | 1 | 0 | 92 | 28 |
| 24 | 1010 | 0.5 | 1 | 0 | 96 | 15 |

The invention has been described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for producing a thiol compound, the process comprising:
1) contacting:
 a) an olefin compound;
 b) $H_2S$;
 c) diphenylamine and/or a phenol compound comprising BHT, carvacrol, 2,2'-ethylidene-bis(4,6-di-tert-butylphenol), pentaerythritol tetrakis(3,5-di-tert-butyl-4-hydroxyhydrocinnamate), or any combination thereof; and
 d) a photoinitiator and/or a free radical initiator; and
2) forming the thiol compound.

Aspect 2. The process defined in aspect 1, wherein a molar ratio of $H_2S$ to carbon-carbon double bonds of the olefin compound is in any range of molar ratios disclosed herein, e.g., from about 2:1 to about 500:1, from about 2:1 to about 150:1, from about 2:1 to about 50:1, from about 3:1 to about 50:1, from about 10:1 to about 50:1, from about 5:1 to about 35:1, from about 8:1 to about 25:1, or from about 25:1 to about 250:1.

Aspect 3. The process defined in any one of the preceding aspects, wherein the photoinitiator is present at an amount within any weight percentage range disclosed herein, e.g., from about 0.05 wt. % to about 5 wt. %, from about 0.1 wt. % to about 2 wt. %, from about 0.1 wt. % to about 1 wt. %, from about 0.2 wt. % to about 1 wt. %, or from about 0.05 wt. % to about 0.8 wt. %, based on the weight of the olefin compound.

Aspect 4. The process defined in any one of the preceding aspects, wherein the free radical initiator is present at an amount within any weight percentage range disclosed herein, e.g., from about 0.05 wt. % to about 5 wt. %, from about 0.1 wt. % to about 2 wt. %, from about 0.1 wt. % to about 1 wt. %, from about 0.2 wt. % to about 1 wt. %, or from about 0.05 wt. % to about 0.8 wt. %, based on the weight of the olefin compound.

Aspect 5. A process for producing a sulfide compound, the process comprising:

I) contacting:
A) an olefin compound;
B) a mercaptan compound; and
C) diphenylamine and/or a phenol compound comprising BHT, carvacrol, 2,2'-ethylidene-bis(4,6-di-tert-butylphenol), pentaerythritol tetrakis(3,5-di-tert-butyl-4-hydroxyhydrocinnamate), or any combination thereof; and
II) forming the sulfide compound.

Aspect 6. The process defined in aspect 5, wherein a molar ratio of —SH of the mercaptan compound to carbon-carbon double bonds of the olefin compound is in any range of molar ratios disclosed herein, e.g., from about 10:1 to about 1:10, from about 5:1 to about 1:5, from about 2:1 to about 1:2, from about 1.5:1 to about 1:1.5, from about 1.2:1 to about 1:1.2, from about 1.1:1 to about 1:1.1, or from about 1:1.05 to about 1:1.2.

Aspect 7. The process defined in aspect 5 or 6, wherein a photoinitiator is present in step I) at an amount within any weight percentage range disclosed herein, e.g., from about 0.05 wt. % to about 5 wt. %, from about 0.1 wt. % to about 2 wt. %, from about 0.1 wt. % to about 1 wt. %, from about 0.2 wt. % to about 1 wt. %, or from about 0.05 wt. % to about 0.8 wt. %, based on the weight of the olefin compound.

Aspect 8. The process defined in aspect 5 or 6, wherein a free radical initiator is present in step I) at an amount within any weight percentage range disclosed herein, e.g., from about 0.05 wt. % to about 5 wt. %, from about 0.1 wt. % to about 2 wt. %, from about 0.1 wt. % to about 1 wt. %, from about 0.2 wt. % to about 1 wt. %, or from about 0.05 wt. % to about 0.8 wt. %, based on the weight of the olefin compound.

Aspect 9. The process defined in any one of aspects 5-8, wherein the mercaptan compound has any number of carbon atoms disclosed herein (e.g., at least 1 carbon atom, at least 2 carbon atoms, or at least 3 carbon atoms), or any range of carbon atoms disclosed herein (e.g., from 1 to 100 carbon atoms, from 2 to 80 carbon atoms, or from 1 to 60 carbon atoms).

Aspect 10. The process defined in any one of aspects 5-9, wherein the mercaptan compound has a number of —SH groups in any range of number of —SH groups disclosed herein, e.g., from 1 to 10, from 2 to 8, or from 1 to 4.

Aspect 11. The process defined in any one of aspects 5-10, wherein the mercaptan compound comprises methyl mercaptan, ethyl mercaptan, n-propyl mercaptan, n-butyl mercaptan, t-butyl mercaptan, n-pentyl mercaptan, phenyl mercaptan, or any combination thereof.

Aspect 12. The process defined in any one of aspects 5-10, wherein the mercaptan compound comprises mercaptomethanol, 2-mercaptoethanol, 3-mercaptopropanol, 4-mercaptobutanol, 5-mercaptopentanol, 6-mercaptohexanol, or any combination thereof.

Aspect 13. The process defined in any one of the preceding aspects, wherein the diphenylamine and/or the phenol compound is present at an amount within any weight percentage range disclosed herein, e.g., from about 0.05 wt. % to about 5 wt. %, from about 0.1 wt. % to about 2 wt. %, from about 0.1 to about 1 wt. %, from about 0.25 wt. % to about 2 wt. %, from about 0.25 wt. % to about 1.5 wt. %, from about 0.2 wt. % to about 0.5 wt. %, or from about 0.5 wt. % to about 1 wt. %, based on the weight of the olefin compound.

Aspect 14. The process defined in any one of aspects 1-13, wherein the olefin compound is a mono-olefin (one olefinic double bond).

Aspect 15. The process defined in any one of aspects 1-13, wherein the olefin compound is a di-olefin (two olefinic double bonds).

Aspect 16. The process defined in any one of aspects 1-13, wherein the olefin compound has from 3 to 5 olefinic double bonds.

Aspect 17. The process defined in any one of aspects 1-16, wherein the olefin compound is a hydrocarbon compound.

Aspect 18. The process defined in any one of aspects 1-13, wherein the olefin compound comprises ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, 1-dodecene, styrene, cyclopentene, cyclohexene, cycloheptene, cyclooctene, or any combination thereof.

Aspect 19. The process defined in any one of aspects 1-13, wherein the olefin compound comprises butadiene, isoprene, cyclobutadiene, cyclopentadiene, cyclohexadiene, cyclooctadiene, norbornadiene, vinylcyclohexene, vinylnorbornene, divinylbenzene, cyclopentadiene dimer, trivinylcyclohexane, trivinylbenzene, cycloheptatriene, dimethyl heptatriene, octatriene, cyclooctatriene, cyclododecatriene, cyclooctatetraene, cyclododecatetraene, a polybutadiene, or any combination thereof.

Aspect 20. The process defined in any one of aspects 1-13, wherein the olefin compound comprises cyclooctadiene, cyclododecatriene, trivinylcyclohexane, or a combination thereof.

Aspect 21. The process defined in any one of aspects 1-13, wherein the olefin compound comprises an unsaturated hydrocarbon terpene compound, e.g., d-limonene, alpha-pinene, or a combination thereof.

Aspect 22. The process defined in any one of aspects 1-13, wherein the olefin compound comprises an unsaturated triglyceride or an unsaturated natural source oil, e.g., soybean oil, corn oil, castor bean oil, canola oil, or a combination thereof.

Aspect 23. The process defined in any one of aspects 1-13, wherein the olefin compound comprises one or more of the following compounds:

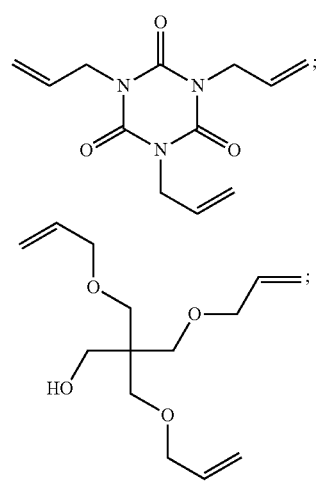

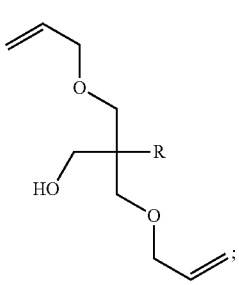

wherein R in formula (A) is any $C_1$-$C_{18}$ hydrocarbyl group disclosed herein.

Aspect 24. The process defined in any one of the preceding aspects, wherein the process further comprises a step of removing at least a portion of the olefin compound, of the $H_2S$ (or the mercaptan compound), of the diphenylamine and/or the phenol compound, of the photoinitiator and/or the free radical initiator, or combinations thereof, from the thiol compound (or from the sulfide compound).

Aspect 25. The process defined in aspect 24, wherein the olefin compound, the $H_2S$ (or the mercaptan compound), the diphenylamine and/or the phenol compound, the photoinitiator and/or the free radical initiator, or combinations thereof, are removed by wiped film evaporation, distillation, short path distillation, or a combination thereof.

Aspect 26. The process defined in any one of the preceding aspects, wherein the thiol compound (or the sulfide compound) is formed at a temperature in any range of temperatures disclosed herein, e.g., from about −30° C. to about 150° C., from about −20° C. to about 130° C., from about 15° C. to about 100° C., from about −5° C. to about 80° C., or from about 0° C. to about 60° C.

Aspect 27. The process defined in any one of the preceding aspects, wherein the thiol compound (or the sulfide compound) is formed in the presence of electromagnetic radiation.

Aspect 28. The process defined in any one of the preceding aspects, wherein the thiol compound (or the sulfide compound) is formed in the presence of ultraviolet light.

Aspect 29. The process defined in any one of aspects 1-26, wherein the thiol compound (or the sulfide compound) is formed in the presence of ultraviolet light and the photoinitiator.

Aspect 30. The process defined in any one of aspects 1-26, wherein the thiol compound (or the sulfide compound) is formed in the presence of the free radical initiator.

Aspect 31. The process defined in aspect 30, wherein the thiol compound (or the sulfide compound) is formed at conditions suitable for a thermal decomposition of the free radical initiator.

Aspect 32. The process defined in any one of the preceding aspects, wherein the thiol compound (or the sulfide compound) is formed in the presence of any solvent disclosed herein, e.g., a hydrocarbon solvent, an aromatic hydrocarbon solvent, a ketone solvent, an alcohol solvent, an ether solvent, or any combination thereof.

Aspect 33. The process defined in any one of the preceding aspects, wherein at least about 65%, at least about 75%, at least about 85%, at least about 90%, or at least about 95%, of the carbon-carbon double bonds of the olefin compound have reacted to form a thiol group (or a sulfide group).

Aspect 34. The process defined in any one of the preceding aspects, wherein the percent conversion of the olefin compound in the process for producing the thiol compound (or in the process for producing the sulfide compound) is greater, by any amount disclosed herein, than the percent conversion obtained by conducting the process without diphenylamine and/or the phenol compound, under the same reaction conditions.

Aspect 35. The process defined in any one of the preceding aspects, wherein the time required to reach a target percent conversion of the olefin compound in the process for producing the thiol compound (or in the process for producing the sulfide compound) is less, by any amount disclosed herein, than the time required to reach the target percent conversion obtained by conducting the process without diphenylamine and/or the phenol compound, under the same reaction conditions.

Aspect 36. The process defined in any one of aspects 1-35, wherein diphenylamine and/or the phenol compound comprise diphenylamine.

Aspect 37. The process defined in any one of aspects 1-35, wherein diphenylamine and/or the phenol compound comprise BHT.

Aspect 38. The process defined in any one of aspects 1-35, wherein diphenylamine and/or the phenol compound comprise carvacrol.

Aspect 39. The process defined in any one of aspects 1-35, wherein diphenylamine and/or the phenol compound comprise 2,2'-ethylidene-bis(4,6-di-tert-butylphenol).

Aspect 40. The process defined in any one of aspects 1-35, wherein diphenylamine and/or the phenol compound comprise pentaerythritol tetrakis(3,5-di-tert-butyl-4-hydroxyhydrocinnamate).

Aspect 41. A thiol compound (or a sulfide compound) produced by the process defined in any one of the preceding aspects.

Aspect 42. An article of manufacture comprising the thiol compound (or the sulfide compound) defined in aspect 36.

I claim:
1. A process for producing a thiol compound, the process comprising:
   i) contacting:
      a) an olefin compound;
      b) $H_2S$;
      c) diphenylamine and/or a phenol compound comprising BHT, carvacrol, 2,2'-ethylidene-bis(4,6-di-tert-butylphenol), pentaerythritol tetrakis(3,5-di-tert-butyl-4-hydroxyhydrocinnamate), or any combination thereof; and
      d) a photoinitiator and/or a free radical initiator; and
   ii) forming the thiol compound.

2. The process of claim 1, wherein a molar ratio of $H_2S$ to carbon-carbon double bonds of the olefin compound is from about 2:1 to about 150:1.

3. The process of claim 1, wherein:
   an amount of diphenylamine and/or the phenol compound is in a range from about 0.1 wt. % to about 1 wt. %, based on the weight of the olefin compound; and
   an amount of the photoinitiator and/or the free radical initiator is in a range from about 0.05 wt. % to about 5 wt. %, based on the weight of the olefin compound.

4. The process of claim 1, wherein the thiol compound is formed in the presence of ultraviolet light.

5. The process of claim 1, wherein the olefin compound comprises ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, 1-dodecene, styrene, cyclopentene, cyclohexene, cycloheptene, cyclooctene, or any combination thereof.

6. The process of claim 1, wherein the olefin compound comprises limonene, butadiene, isoprene, cyclobutadiene, cyclopentadiene, cyclohexadiene, cyclooctadiene, norbornadiene, vinylcyclohexene, vinylnorbornene, divinylbenzene, cyclopentadiene dimer, trivinylcyclohexane, trivinylbenzene, cycloheptatriene, dimethyl heptatriene, octatriene, cyclooctatriene, cyclododecatriene, cyclooctatetraene, cyclododecatetraene, a polybutadiene, or any combination thereof.

7. The process of claim 1, wherein the process comprises:
contacting the olefin compound, $H_2S$, diphenylamine, and the photoinitiator; and
forming the thiol compound in the presence of ultraviolet light;
wherein a percent conversion of the olefin compound is greater than a percent conversion obtained by conducting the process without diphenylamine, under the same reaction conditions.

8. The process of claim 1, wherein the process comprises:
contacting the olefin compound, $H_2S$, butylated hydroxytoluene, and the photoinitiator; and
forming the thiol compound in the presence of ultraviolet light;
wherein a percent conversion of the olefin compound is greater than a percent conversion obtained by conducting the process without butylated hydroxytoluene, under the same reaction conditions.

9. The process of claim 1, wherein the process comprises:
contacting the olefin compound, $H_2S$, carvacrol, and the photoinitiator; and
forming the thiol compound in the presence of ultraviolet light;
wherein a percent conversion of the olefin compound is greater than a percent conversion obtained by conducting the process without carvacrol, under the same reaction conditions.

10. The process of claim 1, wherein the process comprises:
contacting the olefin compound, $H_2S$, 2,2'-ethylidene-bis(4,6-di-tert-butylphenol), and the photoinitiator; and
forming the thiol compound in the presence of ultraviolet light;
wherein a percent conversion of the olefin compound is greater than a percent conversion obtained by conducting the process without 2,2'-ethylidene-bis(4,6-di-tert-butylphenol), under the same reaction conditions.

11. The process of claim 1, wherein the process comprises:
contacting the olefin compound, $H_2S$, pentaerythritol tetrakis(3,5-di-tert-butyl-4-hydroxyhydrocinnamate), and the photoinitiator; and
forming the thiol compound in the presence of ultraviolet light;
wherein a percent conversion of the olefin compound is greater than a percent conversion obtained by conducting the process without pentaerythritol tetrakis(3,5-di-tert-butyl-4-hydroxyhydrocinnamate), under the same reaction conditions.

12. The process of claim 1, wherein a molar percent conversion of the olefin compound is at least about 90%.

13. The process of claim 1, wherein the process further comprises a step of removing at least a portion of the olefin compound, of the $H_2S$, of the diphenylamine and/or the phenol compound, of the photoinitiator and/or the free radical initiator, or combinations thereof, from the thiol compound.

14. A process for producing a sulfide compound, the process comprising:
I) contacting:
A) an olefin compound;
B) a mercaptan compound; and
C) diphenylamine and/or a phenol compound comprising BHT, carvacrol, 2,2'-ethylidene-bis(4,6-di-tert-butylphenol), pentaerythritol tetrakis(3,5-di-tert-butyl-4-hydroxyhydrocinnamate), or any combination thereof; and
II) forming the sulfide compound.

15. The process of claim 14, wherein a molar ratio of —SH of the mercaptan compound to carbon-carbon double bonds of the olefin compound is in a range from about 2:1 to about 1:2.

16. The process of claim 14, wherein the mercaptan compound comprises methyl mercaptan, ethyl mercaptan, n-propyl mercaptan, n-butyl mercaptan, t-butyl mercaptan, n-pentyl mercaptan, phenyl mercaptan, mercaptomethanol, 2-mercaptoethanol, 3-mercaptopropanol, 4-mercaptobutanol, 5-mercaptopentanol, 6-mercaptohexanol, or any combination thereof.

17. The process of claim 14, wherein an amount of diphenylamine and/or the phenol compound is in a range from about 0.1 wt. % to about 1 wt. %, based on the weight of the olefin compound.

18. The process of claim 14, wherein the process comprises:
contacting the olefin compound, the mercaptan compound, diphenylamine, and a photoinitiator and/or free radical initiator; and
forming the sulfide compound in the presence of ultraviolet light;
wherein a percent conversion of the olefin compound is greater than a percent conversion obtained by conducting the process without diphenylamine, under the same reaction conditions.

19. The process of claim 14, wherein the process comprises:
contacting the olefin compound, the mercaptan compound, the phenol compound, and a photoinitiator and/or free radical initiator; and
forming the sulfide compound in the presence of ultraviolet light;
wherein a percent conversion of the olefin compound is greater than a percent conversion obtained by conducting the process without the phenol compound, under the same reaction conditions.

20. The process of claim 14, wherein a molar percent conversion of the olefin compound is at least about 90%.

* * * * *